US010213151B2

(12) United States Patent
Filloux et al.

(10) Patent No.: US 10,213,151 B2
(45) Date of Patent: Feb. 26, 2019

(54) SYSTEMS AND METHODS FOR EVALUATING THE INTEGRITY OF A UTERINE CAVITY

(71) Applicant: Minerva Surgical, Inc., Cupertino, CA (US)

(72) Inventors: Dominique Filloux, Redwood City, CA (US); Dave Clapper, Atherton, CA (US); Akos Toth, Cupertino, CA (US); Sean Darby, San Jose, CA (US); Tejas N. Mazmudar, Palo Alto, CA (US); Estela Hilario, Los Altos, CA (US)

(73) Assignee: Minerva Surgical, Inc., Redwood City, CA (US)

(*) Notice: Subject to any disclaimer, the term of this patent is extended or adjusted under 35 U.S.C. 154(b) by 0 days.

(21) Appl. No.: 15/418,635

(22) Filed: Jan. 27, 2017

(65) Prior Publication Data

US 2018/0214067 A1    Aug. 2, 2018

(51) Int. Cl.
*A61B 5/00*        (2006.01)
*A61B 5/03*        (2006.01)
(Continued)

(52) U.S. Cl.
CPC ............ *A61B 5/4325* (2013.01); *A61B 5/035* (2013.01); *A61B 5/6853* (2013.01); *A61B 5/746* (2013.01); *A61B 18/02* (2013.01); *A61B 18/1492* (2013.01); *A61B 2018/00559* (2013.01); *A61B 2018/00577* (2013.01); *A61B 2018/00642* (2013.01); *A61B 2018/00702* (2013.01);
(Continued)

(58) Field of Classification Search
CPC ..... A61B 5/746; A61B 5/4325; A61B 5/6853; A61B 18/02; A61B 18/1492; A61B 5/035; A61B 2018/0212; A61B 2018/00559; A61B 2018/00642; A61B 2018/00702; A61B 2018/00744; A61B 2018/00577
See application file for complete search history.

(56) References Cited

U.S. PATENT DOCUMENTS 737,131    A      8/1903   Frederick
3,948,259  A  *   4/1976   Bolduc ................. A61F 6/22
                                                       128/831
(Continued)

FOREIGN PATENT DOCUMENTS

WO    WO-2016057545 A1    4/2016
WO    WO-2018140892 A1    8/2018

OTHER PUBLICATIONS

Co-pending U.S. Appl. No. 15/954,491, filed Apr. 16, 2018.
(Continued)

*Primary Examiner* — Rene T Towa
(74) *Attorney, Agent, or Firm* — Wilson Sonsini Goodrich & Rosati

(57) ABSTRACT

A system for accessing a patient's uterine cavity and detecting perforations in the uterus includes an elongated probe having a flow channel extending to a terminal outlet in a distal region of the probe. A fluid source is coupled to the flow channel, and a seal on the probe is positionable in an endocervical canal. The probe may be trans-cervically inserted into the uterine cavity, and a fluid may be introduced through the channel to flow outwardly from the terminal outlet into the uterine cavity. A parameter of said fluid flow is monitored to detect a perforation in the uterus.

29 Claims, 10 Drawing Sheets

(51) Int. Cl.
*A61B 18/00* (2006.01)
*A61B 18/02* (2006.01)
*A61B 18/14* (2006.01)

(52) U.S. Cl.
CPC .............. *A61B 2018/00744* (2013.01); *A61B 2018/0212* (2013.01)

(56) References Cited

U.S. PATENT DOCUMENTS

| | | | |
|---|---|---|---|
| 4,979,948 A | 12/1990 | Geddes et al. | |
| 5,191,883 A | 3/1993 | Lennox et al. | |
| 5,769,880 A | 6/1998 | Truckai et al. | |
| 5,776,129 A | 7/1998 | Mersch | |
| 5,827,273 A | 10/1998 | Edwards | |
| 5,891,134 A | 4/1999 | Goble et al. | |
| 5,925,038 A | 7/1999 | Panescu et al. | |
| 6,041,260 A | 3/2000 | Stern et al. | |
| 6,296,639 B1 | 10/2001 | Truckai et al. | |
| 6,508,815 B1 | 1/2003 | Strul et al. | |
| 6,663,626 B2 | 12/2003 | Truckai et al. | |
| 6,736,811 B2 | 5/2004 | Panescu et al. | |
| 6,813,520 B2 | 11/2004 | Truckai et al. | |
| 7,371,231 B2 | 5/2008 | Rioux et al. | |
| 8,197,476 B2 | 6/2012 | Truckai | |
| 8,197,477 B2 | 6/2012 | Truckai | |
| 8,343,878 B2 | 1/2013 | Qiu et al. | |
| 8,372,068 B2 | 2/2013 | Truckai | |
| 8,382,753 B2 | 2/2013 | Truckai | |
| 8,394,037 B2 * | 3/2013 | Toth | A61B 5/035 600/560 |
| 8,500,732 B2 | 8/2013 | Truckai et al. | |
| 8,540,708 B2 | 9/2013 | Truckai et al. | |
| 8,690,873 B2 | 4/2014 | Truckai et al. | |
| 8,821,486 B2 | 9/2014 | Toth et al. | |
| 8,939,971 B2 | 1/2015 | Truckai et al. | |
| 9,050,102 B2 | 6/2015 | Truckai | |
| 2003/0060800 A1 * | 3/2003 | Ryan | A61M 25/01 604/515 |
| 2005/0143728 A1 * | 6/2005 | Sampson | A61B 18/00 606/41 |
| 2005/0240211 A1 * | 10/2005 | Sporri | A61B 17/42 606/193 |
| 2007/0088344 A1 * | 4/2007 | Schechter | A61B 18/02 606/21 |
| 2008/0097425 A1 | 4/2008 | Truckai | |
| 2008/0167664 A1 * | 7/2008 | Payne | A61M 13/003 606/135 |
| 2009/0054892 A1 | 2/2009 | Rioux et al. | |
| 2010/0198214 A1 | 8/2010 | Layton, Jr. et al. | |
| 2010/0228239 A1 | 9/2010 | Freed | |
| 2013/0310705 A1 | 11/2013 | Toth | |
| 2015/0173826 A1 | 6/2015 | Churchill et al. | |
| 2015/0289920 A1 | 10/2015 | Burnett et al. | |
| 2015/0366607 A1 | 12/2015 | Bek et al. | |
| 2016/0331444 A1 | 11/2016 | Truckai et al. | |

OTHER PUBLICATIONS

PCT/US2018/015774 International Search Report dated May 30, 2018.
"Office Action dated Aug. 6, 2018 for U.S. Appl. No. 15/954,491."

* cited by examiner

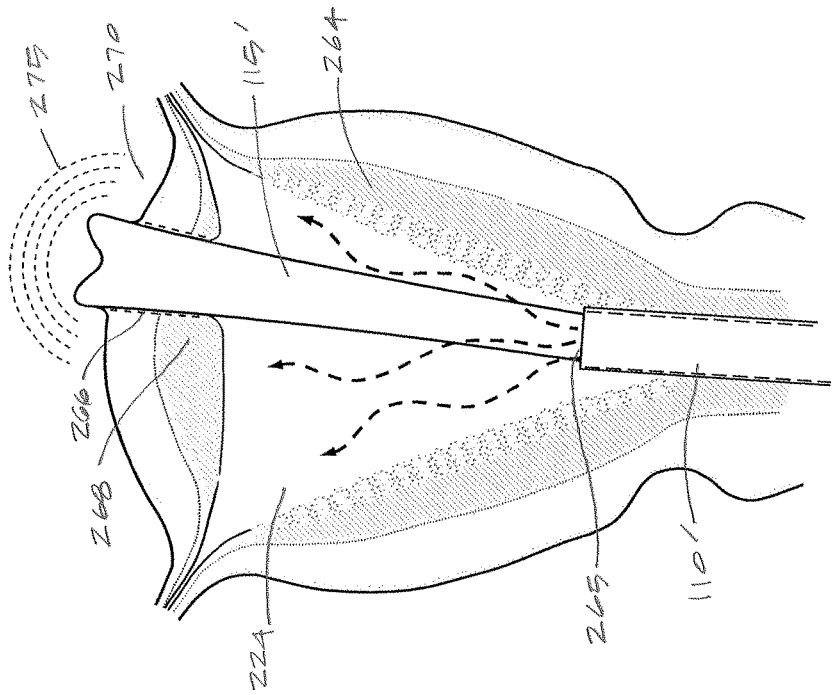
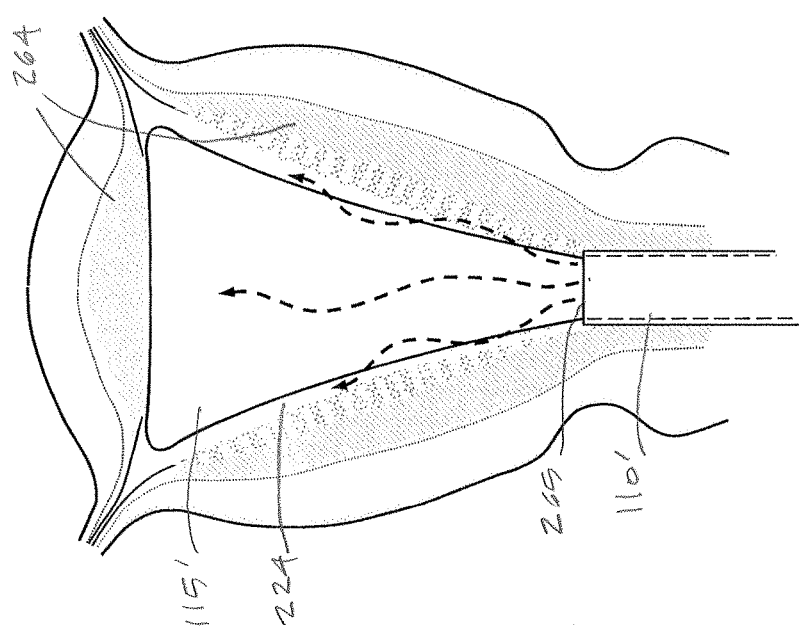
FIG. 5A
(PRIOR ART)
FIG. 5B
(PRIOR ART)

SYSTEMS AND METHODS FOR EVALUATING THE INTEGRITY OF A UTERINE CAVITY

BACKGROUND OF THE INVENTION

1. Field of the Invention

The present invention relates to systems and methods for global endometrial ablation in a treatment of menorrhagia. More particularly, the present invention relates to a subsystem using gas flows and a controller to test whether a patient's uterine cavity has a wall that is perforated or whether the uterus is intact, wherein such a test should be performed before proceeding with an ablation procedure.

A variety of devices have been proposed for endometrial ablation. Of relevance to the present invention, a variety of radiofrequency ablation devices have been proposed including solid electrodes, balloon electrodes, metalized fabric electrodes, and the like. While often effective, many of the prior electrode designs have suffered from one or more deficiencies, such as relatively slow treatment times, incomplete treatments, non-uniform ablation depths, and risk of injury to adjacent organs.

For these reasons, it would be desirable to provide systems and methods that allow for endometrial ablation using radiofrequency current which is rapid, provides for controlled ablation depth and which reduce the risk of injury to adjacent organs. At least some of these objectives will be met by the invention described herein.

2. Description of the Background Art

U.S. Pat. Nos. 5,769,880; 6,296,639; 6,663,626; and 6,813,520 describe intrauterine ablation devices formed from a permeable mesh defining electrodes for the application of radiofrequency energy to ablate uterine tissue. U.S. Pat. No. 4,979,948 describes a balloon filled with an electrolyte solution for applying radiofrequency current to a mucosal layer via capacitive coupling. US 2008/097425, having common inventorship with the present application, describes delivering a pressurized flow of a liquid medium which carries a radiofrequency current to tissue, where the liquid is ignited into a plasma as it passes through flow orifices. U.S. Pat. No. 5,891,134 describes a radiofrequency heater within an enclosed balloon. U.S. Pat. No. 6,041,260 describes radiofrequency electrodes distributed over the exterior surface of a balloon which is inflated in a body cavity to be treated. U.S. Pat. No. 7,371,231 and US 2009/054892 describe a conductive balloon having an exterior surface which acts as an electrode for performing endometrial ablation. U.S. Pat. No. 5,191,883 describes bipolar heating of a medium within a balloon for thermal ablation. U.S. Pat. No. 6,736,811 and U.S. Pat. No. 5,925,038 show an inflatable conductive electrode.

BRIEF SUMMARY OF THE INVENTION

The following presents a simplified summary of some embodiments of the invention in order to provide a basic understanding of the invention. This summary is not an extensive overview of the invention. It is not intended to identify key/critical elements of the invention or to delineate the scope of the invention. Its sole purpose is to present some embodiments of the invention in a simplified form as a prelude to the more detailed description that is presented later.

The present invention provides methods, systems and devices for evaluating the integrity of a uterine cavity. The uterine cavity may be perforated or otherwise damaged by the transcervical introduction of probes and instruments into the uterine cavity. If the uterine wall is perforated, it would be preferable to defer any ablation treatment until the uterine wall is healed. A method of the invention comprises introducing transcervically a probe into a patient's uterine cavity, providing a flow of a fluid (e.g., $CO_2$) through the probe into the uterine cavity and monitoring the rate of the flow to characterize the uterine cavity as perforated or non-perforated based on a change in the flow rate. If the flow rate drops to zero or close to zero, this indicates that the uterine cavity is intact and not perforated. If the flow rate does not drop to zero or close to zero, this indicates that a fluid flow is leaking through a perforation in the uterine cavity into the uterine cavity or escaping around an occlusion balloon that occludes the cervical canal.

Embodiments herein provide a method of characterizing a patient's uterus, which can comprise introducing a flow of a fluid into a uterine cavity of a patient and monitoring the flow to characterize the uterine cavity as at least one of perforated or non-perforated based on a change in a rate of the flow. The introducing step may include, for example, trans-cervically introducing a probe into the uterine cavity and introducing the flow through the probe.

Monitoring may include providing a signal, responsive to the rate of flow, that characterizes the uterine cavity as at least one of perforated or non-perforated. As an example, monitoring may include generating a signal responsive to the rate of flow not dropping below a predetermined level, the signal characterizing the uterine cavity as perforated. In embodiments, the predetermined level may be in the range of 0.01 slpm to 1.0 slpm, and more often between 0.01 spl, and 0.05 slpm.

In embodiments, monitoring comprises generating a signal responsive to the rate of flow dropping below a predetermined level, the signal characterizing the uterine cavity as non-perforated. The predetermined level may be, for example, 0.02 slpm.

In further embodiments, monitoring comprises monitoring a rate of flow after a predetermined first interval after initiation of the flow. The first interval may be, as examples, at least 5 seconds, at least 15 seconds, or at least 30 seconds.

Monitoring may additionally include monitoring a rate of flow over a second predetermined interval after the first interval. The second interval may be a least 1 second, at least 5 seconds, or at least 10 seconds, as examples.

In additional embodiments, monitoring includes providing a signal, responsive to the rate of flow, that characterizes the uterine cavity as at least one of perforated or non-perforated, and wherein the signal is at least one of visual, aural and tactile.

In embodiments, prior to introducing the flow, a member is positioned within the cervical canal that substantially prevents a flow of the fluid out of the uterine cavity. Introducing may include transcervically introducing a probe into the uterine cavity, and introducing the flow through the probe, with the member positioned about an exterior of the probe. The member may be expanded in the cervical canal.

In embodiments, the fluid is a gas or a liquid.

In additional embodiments, introducing includes transcervically introducing a probe into the uterine cavity, and introducing the flow through the probe. The probe has a working end with an energy-delivery surface for ablating uterine cavity tissue. Responsive to the uterine cavity being characterized as perforated, energy delivery surface is disabled. Alternatively or additionally, responsive to the uterine cavity being characterized as non perforated, activation of the energy delivery surface may be enabled or even caused to happen automatically.

In embodiments, a method of endometrial ablation is provided, the method including introducing an ablation probe into a uterine cavity of a patient, flowing a fluid from a fluid source through the probe into the uterine cavity, monitoring the rate of the flow of the fluid into the uterine cavity to characterize the cavity as at least one of perforated or non-perforated based on a change in the flow rate, and responsive the to the uterine cavity being characterized as non perforated, activating the ablation probe to ablate an interior of the uterine cavity.

For a fuller understanding of the nature and advantages of the present invention, reference should be made to the ensuing detailed description and accompanying drawings.

BRIEF DESCRIPTION OF THE DRAWINGS

In order to better understand the invention and to see how it may be carried out in practice, some preferred embodiments are next described, by way of non-limiting examples only, with reference to the accompanying drawings, in which like reference characters denote corresponding features consistently throughout similar embodiments in the attached drawings.

FIG. 5A is a schematic view of a prior art method of testing uterine integrity, including introducing an energy applicator into a patient's uterine cavity, expanding the energy applicator, actuating a gas flow from the introducer sleeve into the uterine cavity, and monitoring at least one gas flow parameter to determine that there is no perforation in a uterine cavity wall.

FIG. 5B is a schematic view of a prior art method of testing uterine integrity similar to that of FIG. 5A, except FIG. 5B indicates that the energy applicator has penetrated the fundus, and potentially plugs the perforation so that gas flow does not exit the perforation which results in characterizing the uterus as non-perforated when there is a perforation.

FIG. 7A is a schematic view of another variation of a system and method of the invention that monitors uterine integrity, wherein the elongated probe functions as a sound for measuring uterine cavity length while at the same time using fluid flows through the probe as in previous embodiments, wherein FIG. 7A depicts a non-perforated uterine cavity.

DETAILED DESCRIPTION

In the following description, various embodiments of the present invention will be described. For purposes of explanation, specific configurations and details are set forth in order to provide a thorough understanding of the embodiments. However, it will also be apparent to one skilled in the art that the present invention may be practiced without the specific details. Furthermore, well-known features may be omitted or simplified in order not to obscure the embodiments being described.

In general, an endometrial ablation system is described herein that comprises an elongated introducer member for accessing a patient's uterine cavity with a working end that deploys an energy applicator comprising an expandable thin-wall dielectric structure adapted to contain a gas. In one variation, an interior chamber of the thin-wall dielectric structure or array contains a circulating neutral gas such as argon. An RF power source provides current that is coupled to the neutral gas flow by a first polarity electrode disposed within the interior chamber and a second polarity electrode at an exterior of the dielectric structure. The circulating gas flow, which is converted to a conductive plasma within the array by the electrode arrangement, permits current flow through engaged endometrial tissue only when the voltage across the combination of the then-ionized gas or plasma, the thin-wall dielectric structure and the engaged tissue reaches a threshold that causes capacitive coupling across the thin-wall dielectric material. The conductive plasma heats the dielectric wall which in turn conducts heat to the tissue in contact with the array. This electrosurgical ablation system is described in more detail in the following commonly owned and/or licensed U.S. Pat. Nos. 9,050,102; 8,939,971; 8,821,486; 8,690,873; 8,540,708; 8,500,732; 8,382,753; 8,372,068; 8,343,878; 8,197,477 and 8,197,476, all of which are incorporated herein by this reference.

Figure 1:
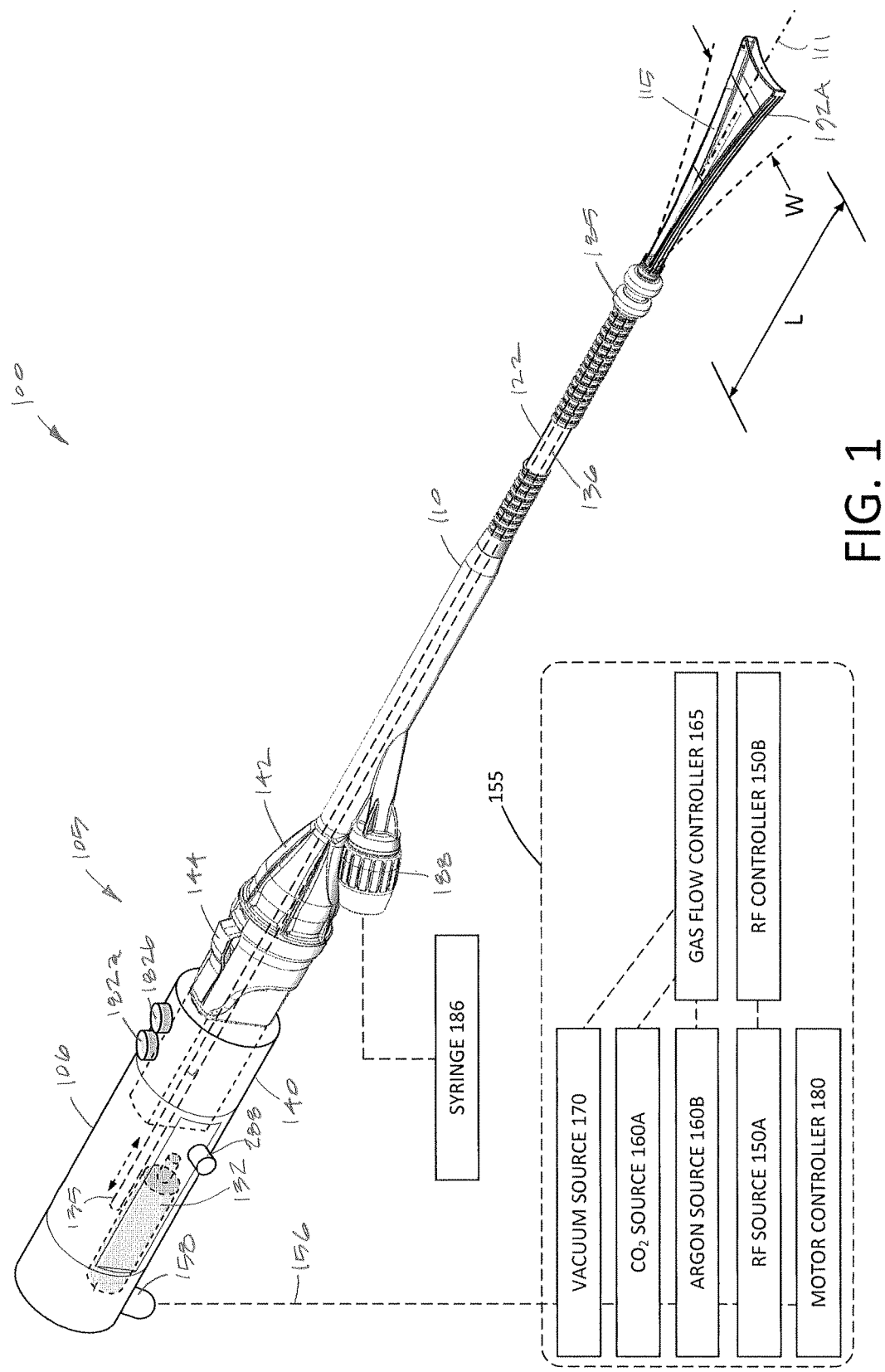
FIG. 1 is a perspective view of an ablation system corresponding to the invention, including a hand-held electrosurgical device for endometrial ablation and a block diagram showing an RF power source, an RF controller, a $CO_2$ gas source, an argon gas source, a gas flow controller and an electrical source and controller for a motor carried by the hand-held device.

FIG. 1 depicts one embodiment of an electrosurgical ablation system 100 configured for endometrial ablation. The system 100 includes a hand-held device 105 with a proximal handle 106 shaped for grasping with a human hand that is coupled to an elongated shaft or introducer 110 extending about longitudinal axis 111 to a distal portion that comprises an energy applicator or expandable body 115. The introducer 110 can be fabricated of a thin-wall plastic, composite or metal in a round or oval cross-section having a diameter or major axis ranging from about 3 mm to 8 mm and a length suited for trans-cervical access to a patient's uterine cavity. The handle 106 is shown in an in-line configuration in FIG. 1, but any type of pistol grip or other handle design is possible.

Figure 2:
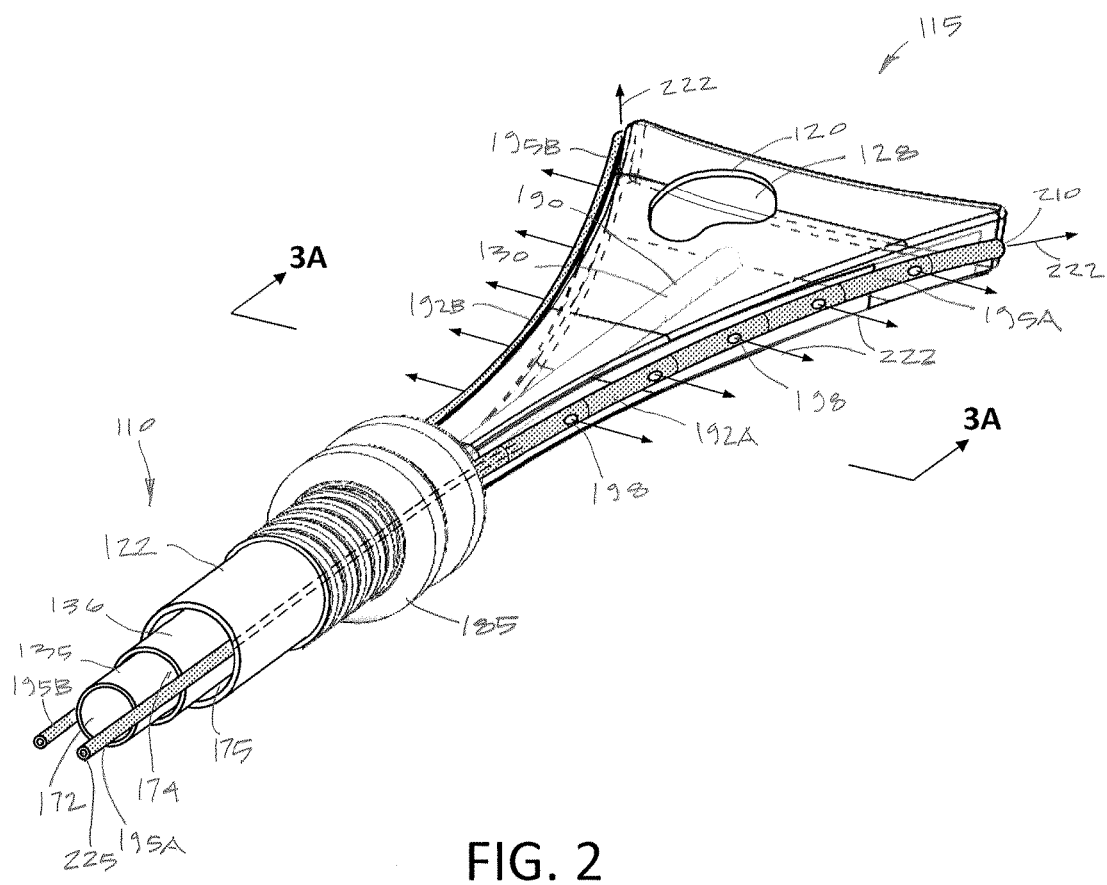
FIG. 2 is a perspective view of the distal energy applicator or working end of the hand-held electrosurgical device of FIG. 1 with the energy applicator comprising an expanded thin-wall dielectric structure including flow channels extending along sides of the dielectric structure.

Referring to FIG. 2, the energy applicator 115 consists of a structure comprising a flexible or elastomeric thin wall material 120 that can be expanded to a range of triangular shapes as indicated by phantom shape 125 of FIG. 1. The thin wall 120 is a dielectric material and can be collapsed or constrained at least partially within an outer sleeve 122 of the introducer 110. Such a triangular shape is configured for substantially contacting the endometrial lining of a patient's uterus that is targeted for ablation. In one variation, the energy applicator 115 comprises a thin wall silicone material having a thickness ranging between 0.005" and 0.020" surrounding a fluid-tight interior chamber 128. The energy applicator 115 can be expanded to a range of widths wherein the width W in FIG. 1 shows a pre-expanded width. The expansion mechanism for expanding the energy applicator 115 can be an expandable-collapsible frame structure 130 as described in U.S. Pat. No. 9,050,102 referenced above. In the embodiment shown in FIG. 1, an electrical motor 132 is provided to actuate the expandable-collapsible frame 130 (partially shown) in interior chamber 128, which differs from the embodiment of U.S. Pat. No. 9,050,102 referenced above. The motor 132 of FIG. 1 is utilized to move a first inner sleeve 135 relative to second inner sleeve 136 (see FIG. 2) to expand or collapse the frame 130 and energy applicator 115. It can be easily understood that the motor 132 can be coupled to a gear reduction mechanism and a linear drive mechanism (not shown) to actuate the expandable-collapsible frame that is described in U.S. Pat. No. 9,050,102 and the other commonly-owned patents referenced above.

In FIG. 1, the handle 106 can be fabricated of an electrically insulative material such as a molded plastic with first and second portions, 140 and 142, wherein the second portion 142 is coupled to outer sleeve 122. It can be seen that second portion 142 is slidable relative to axis 111 into first portion 140 of handle 106. A latching mechanism 144 is adapted to lock the first and second handle portions 140 and 142 in a selected axial relationship. By this means, the outer sleeve 122 of the introducer 110 can be axially translated relative to concentric inner sleeves 135 and 136 (see FIG. 2) that carry the frame 130 and energy applicator 115 to thereby provide a selected length L (see FIG. 1) of the energy applicator 115 when expanded in a uterine cavity.

FIG. 1 further shows that the system 100 includes an RF energy source 150A and RF controller 150B in a console or control unit 155. The RF energy source 150A is connected to the hand-held device 105 by a flexible conduit 156 with a plug-in connector 158 that carries electrical leads that couple to an electrode arrangement in the applicator head or energy applicator 115 as described in detail in U.S. Pat. No. 9,050,102 referenced above. The control unit 155 is further adapted to carry first and second fluid or gas sources 160A, 160B and a gas flow controller 165 for controlling gas flows.

The first fluid or gas source 160A can be a $CO_2$ cartridge which provides a $CO_2$ flow to flow channels at the surface of the energy applicator 115 for testing the integrity and non-perforation of the walls of the uterine cavity as will be described below. The second gas source 160B is an argon gas cartridge which provides the neutral gas for circulating in interior chamber 128 of the dielectric structure that is ionized into a plasma as described in detail in U.S. Pat. No. 9,050,102 referenced above. The gas flow controller 165 is further configured to control a vacuum or negative pressure source 170 in communication with the interior chamber 128 of the energy applicator, and optionally to the exterior of the energy applicator 115. The fluid flow pathways in the system include flow channels in the conduit 156 that extends from the control unit 155 to the hand-held device 105. The flow channels and pathways in the elongate introducer 110 are indicated at 172, 174 and 175 in FIG. 2. Flow channels 174 and 172 provide gas inflows and outflows, respectively, to and from the interior chamber 128 of the energy applicator 115. Flow channel 175 is adapted for providing a pathway to or from the uterine cavity around an exterior of the energy applicator 115, for example the removal of gas or liquid from the uterine cavity.

Still referring to FIG. 1, the console or control unit 155 includes a motor electrical source/controller 180 for operating the motor 132 to actuate the expandable-collapsible frame 130. In one variation, the handle 106 has first and second actuator buttons 182a and 182b for expanding and collapsing, respectively, the frame 130 in the interior of the energy applicator 115. It should be appreciated that any type of joystick, rocker switch, trigger, foot pedal or the like may be used to actuate the expandable-collapsible frame and energy applicator 115.

FIGS. 1 and 2 further show a cervical sealing balloon 185 extending along a length of the introducer 110. As can be seen in FIG. 1, the block diagram includes a syringe 186 that can be coupled to fitting 188 and the handle 106 and is adapted for inflating the expandable sealing balloon 185 as described further below.

Now turning to the electrosurgical aspects of the invention, referring again to FIG. 2, the energy applicator 115 is of the type described in detail in U.S. Pat. No. 9,050,102 and other commonly owned patents referenced above. FIG. 2 illustrates the energy applicator 115 and a cut-away view of the introducer 110 and concentric sleeve assembly thereof. The frame 130 (partially shown) in the interior chamber 128 of the energy applicator 115 comprises a first polarity electrode 190. The energy applicator 115 carries exterior or second polarity electrodes 192A and 192B extending along the sides of the triangular shaped applicator body. The opposing polarity electrodes at the interior and exterior of the dielectric structure (190 and 192A-192B) are configured to convert a flow of neutral gas in chamber 128 into a plasma and to allow capacitive coupling of current through the thin dielectric wall 120 of the applicator body.

Figure 3A:
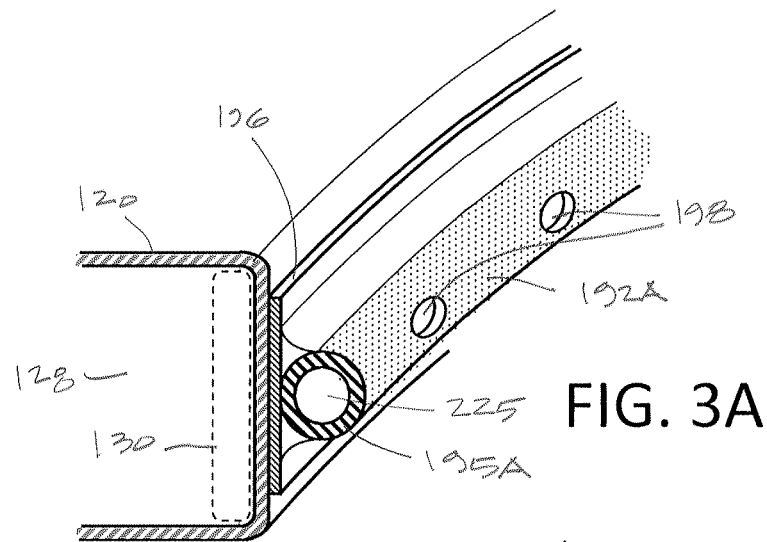
FIG. 3A is an enlarged cut-away view of a side of dielectric structure and a flow channel further depicting an electrode surface.

In the variation shown in FIGS. 1 and 2, the exterior electrodes 192A and 192B consist of a conductive electroless plating on flow channel sleeves 195A and 195B that are used to supply $CO_2$ inflows into a patient's uterine cavity to test for uterine wall perforations as will be described further below. FIG. 3A shows an enlarged sectional view of flow channel sleeve 195A of FIG. 2 wherein the sleeve is bonded to insulator layer 196 with adhesive layer 197. The insulator layer 196 can be Kapton® tape, which in turn is bonded to the thin dielectric wall 120 of the applicator body 115. A plurality of flow outlets 198 are provided along the length of the flow channel sleeves. Such flow outlets can be oriented to face laterally and/or upward and downward along the length thereof, as laterally facing flow channels may be pressed into tissue and occluded.

Figure 3B:
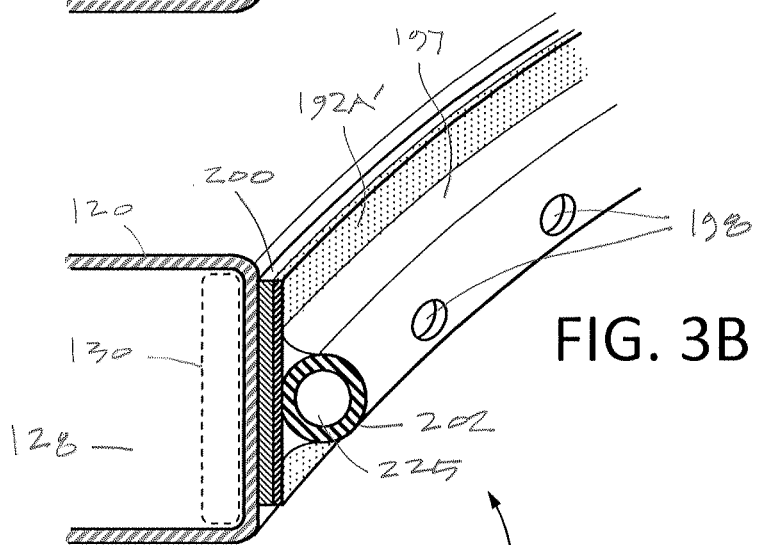
FIG. 3B is an enlarged cut-away view of the dielectric structure similar to that of FIG. 3A showing another variation of a flow channel and electrode arrangement.
Figure 3C:
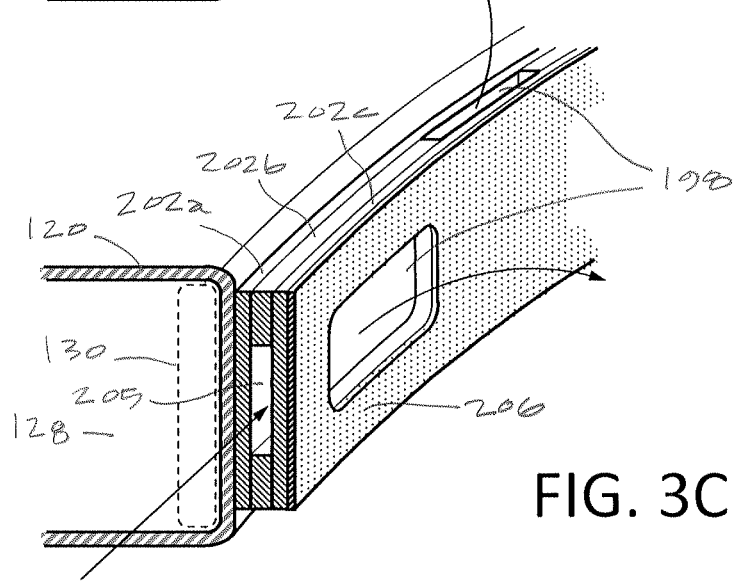
FIG. 3C is another cut-away view of the dielectric structure similar to that of FIGS. 3A-3B showing yet another variation of a flow channel and electrode arrangement.

FIGS. 3B and 3C illustrate other assemblies that provide a flow channel and electrode along an edge of the applicator body 115. FIG. 3B shows the edge of the thin dielectric wall 120 with the Kapton® insulator tape 200 bonded to the exterior of the wall. In this variation, the insulator tape 200 has a conductive plating that comprises the second polarity electrode 192A'. A separate small diameter polymer flow channel sleeve 202 is then bonded with adhesive 197 to the surface of the insulator tape 198 and electrode layer 192A'. FIG. 3C shows an alternative embodiment in which layers of insulator tape 202a, 202b and 202c are bonded to one another with an interior channel in 205 in the middle of the tape assembly that provides the interior flow channel 205. An electrode surface layer 206 is provided over the insulator layers 202a-202c. In this variation, flow outlets 198 are shown facing both laterally and upwardly. Such as assembly also can be constructed of a flexible PCB (printed circuit board).

Still referring to FIG. 2, as described further below, the tubular flow channel sleeves 195A and 195B are multi-functional and are further utilized for testing for a perforation in a patient's uterine wall. Each flow channel sleeve 195A and 195B in this variation has a plurality of outlets 198 as mentioned above along the length of each sleeve and a terminal outlet 210 at the distal end of each sleeve. As shown in FIG. 2, the flow channel sleeves 195A and 190B extend proximately through the interior of introducer 110 and communicate with the $CO_2$ source 160A (see FIG. 1). Thus, it can be seen that $CO_2$ flows indicated by arrows 222 in FIG. 2 can exit the outlets 198 and 210 into a patient's uterine cavity 224 after deployment of the energy applicator 115. The flow pathway 225 in each sleeve 195A and 195B (see FIG. 2) can have a diameter or mean cross-section ranging between about 0.01 mm and 1.0 mm.

In general, the system and methods of the invention allow for the evaluation of the integrity of the patient's uterine cavity which may be perforated or otherwise damaged by the transcervical introduction of probes, sounds and/or other instruments into a uterine cavity. If the uterine wall is perforated, it would be preferable or necessary to defer any ablation treatment until the uterine wall is healed. Thus, a method described in U.S. Pat. No. 8,343,078 and in the other commonly-owned patents referenced above, consists of introducing trans-cervically an introducer into a patient's uterine cavity, expanding a sealing balloon in the endocervical canal, providing a flow of a fluid (e.g., $CO_2$) through the introducer into the uterine cavity and monitoring one or more parameters of the $CO_2$ flow which allow for characterization of the uterine cavity as either perforated or non-perforated based on an evaluation of a selected gas flow parameter.

Figure 4:
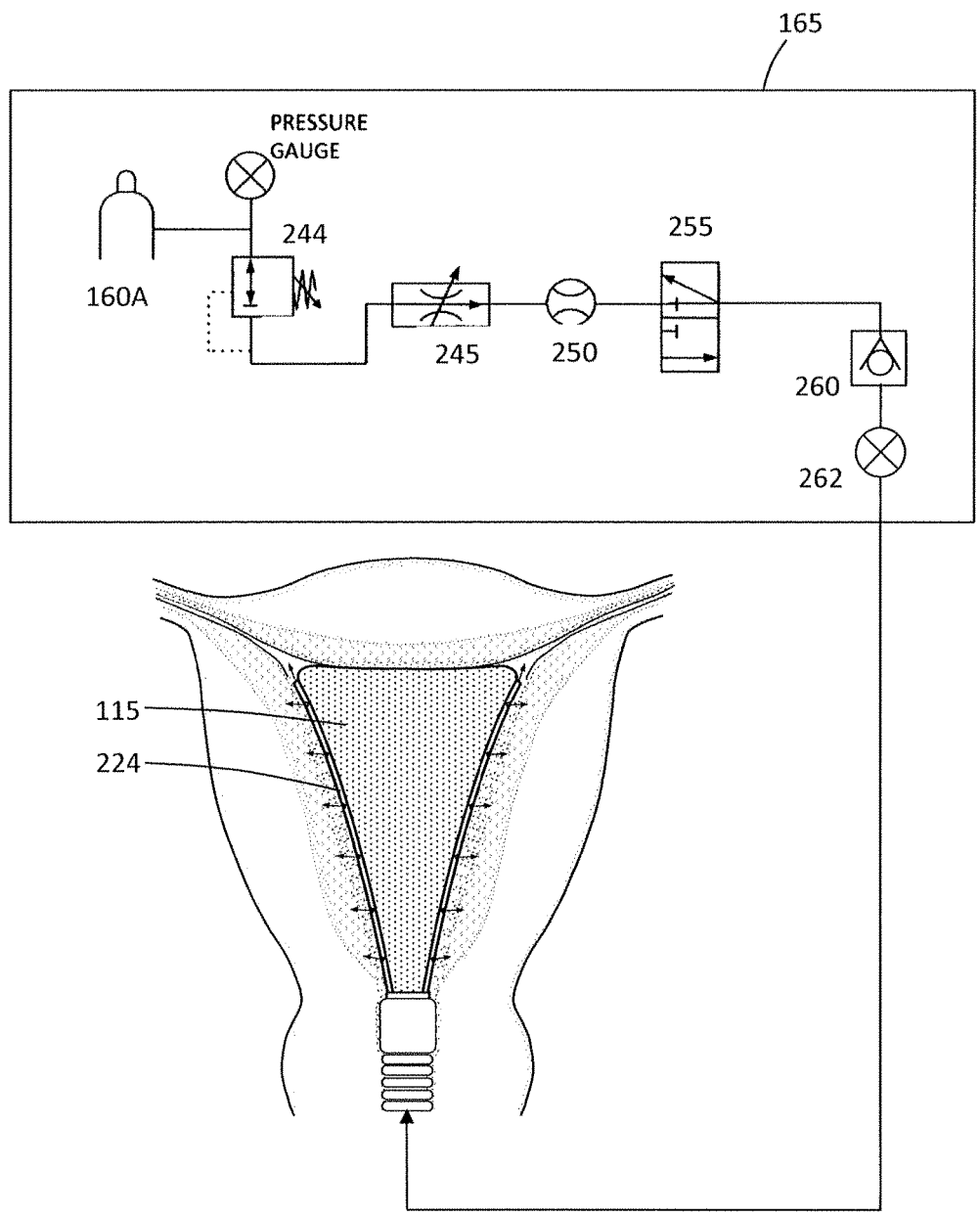
FIG. 4 is a block diagram of the gas flow components of the controller unit of FIG. 1.

FIG. 4 is a block diagram that schematically depicts the system components that are related to the cavity integrity test subsystem only. These components include the gas flow controller 165 that provides the flow of $CO_2$ through the hand-held probe 105 and introducer 110 to flow channel sleeves 195A and 195B (FIG. 2) and the pressurized $CO_2$ source 240, which can be a disposable $CO_2$ canister. The $CO_2$ source 240 communicates with a downstream pressure regulator 244, an optional proportional valve 245, a flow meter 250, a normally closed solenoid valve 255 and one-way valve 260 for preventing venting of $CO_2$ through valve 255. Upon actuation or the valve 255 by the physician, a flow of $CO_2$ gas can be provided from $CO_2$ source 240 at a predetermined flow rate and pressure through the hand-held device 105 and into the uterine cavity 224. As will be described below, the controller can have control algorithms to monitor the flow rate with flowmeter 250 to determine whether there is a perforation in a wall of the uterine cavity. Alternatively, the pressure sensor 262 shown in FIG. 4 can be used to test for perforations as is known in the art.

Before describing the method of using the system described above and shown in FIGS. 1 and 2, it is useful to describe a typical prior art system that has been developed for uterine perforation detection. FIGS. 5A and 5B illustrate a prior art method of testing for uterine cavity integrity and further shows the potential deficiencies in such a prior art system. In FIG. 5A, it can be seen that the prior art introducer 110' and energy applicator 115' (similar to the type shown in FIGS. 1-2) has been inserted into the uterine cavity 224 and the energy applicator 115' has been expanded. Prior to inserting the introducer 110' into the uterine cavity, the physician used an elongate probe called a uterine sound (not shown) to determine the length of the uterine cavity 224. At times, the physician's initial use of such a probe or sound can cause damage to, or perforation of, the uterine wall 264. At times, an irregular uterine shape will contribute to such damage or perforation of a uterine wall 264. Thus, a key objective of a uterine cavity integrity test is to determine whether the physician's use of a probe or sound has caused such a perforation. In FIG. 5A, it is assumed that no perforation resulted from the physician using the probe or sound. It can be seen that the $CO_2$ gas flows outwardly from the distal end 265 of the introducer 110' and fills the uterine cavity 224 around the exterior of the expanded energy applicator 115'. In this situation, the use of a flow meter, a pressure sensor or a gas volume meter can be utilized to characterize the uterine wall 264 as non-perforated as is known in the prior art.

In FIG. 5B, it is assumed that the physician's use of the probe or sound resulted in a perforation 266 in the fundus portion 268 of the uterine wall 264. Further, FIG. 5B shows that the physician's insertion of the energy applicator 115' followed the path of the sound through the perforation 265 in the fundus 268. Thereafter, the $CO_2$ gas flow is initiated in the manner described previously. In this situation, either of two things may occur. First, it is possible that $CO_2$ will escape the uterine cavity 224 around the energy applicator 115' outwardly through perforation 265 and into the uterine cavity 270, which can be detected by monitoring at least one flow parameter (flow rate, gas pressure, gas volume). Thus, the perforation 266 will be detected by the system and the physician will not proceed with the ablation procedure. However, a second outcome is possible when the energy applicator 115' effectively occludes or seals the perforation 266 since the cross-section of energy applicator 115' can effectively plug such a perforation 266. In this situation, the $CO_2$ flow outwardly from the introducer 110' into the uterine cavity would be monitored and the uterine cavity 224 could be characterized as non-perforated, when in fact there is a perforation 266. If this scenario were to occur, the further actuation of the energy applicator 115', with energy emission indicated at 275 in FIG. 5B, would likely cause thermal injury to organs within the abdominal cavity 270 outside the fundus 268. Such an injury to organs in the patient's abdominal cavity 270 could be very serious and potentially life-threatening.

Figure 6A:
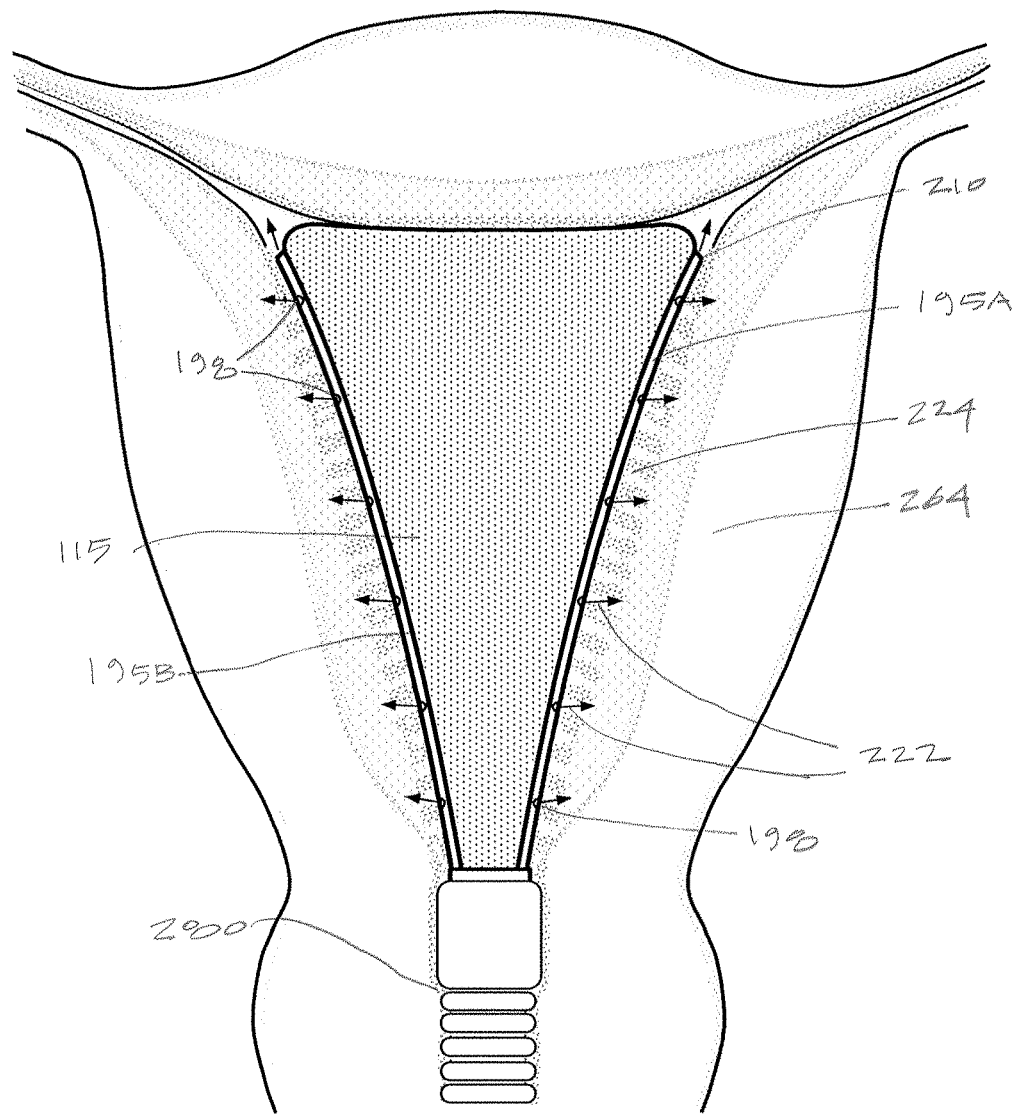
FIG. 6A is a schematic view of the system and method corresponding to the invention for testing uterine cavity integrity, wherein FIG. 6A includes steps of introducing an energy applicator into a patient's uterine cavity, expanding a sealing balloon in the endocervical canal, expanding the energy applicator, actuating a gas flow that exits the energy applicator through flow outlets along its entire length, and monitoring at least one gas flow parameter to determine that there is no perforation in a uterine cavity wall.
Figure 6B:
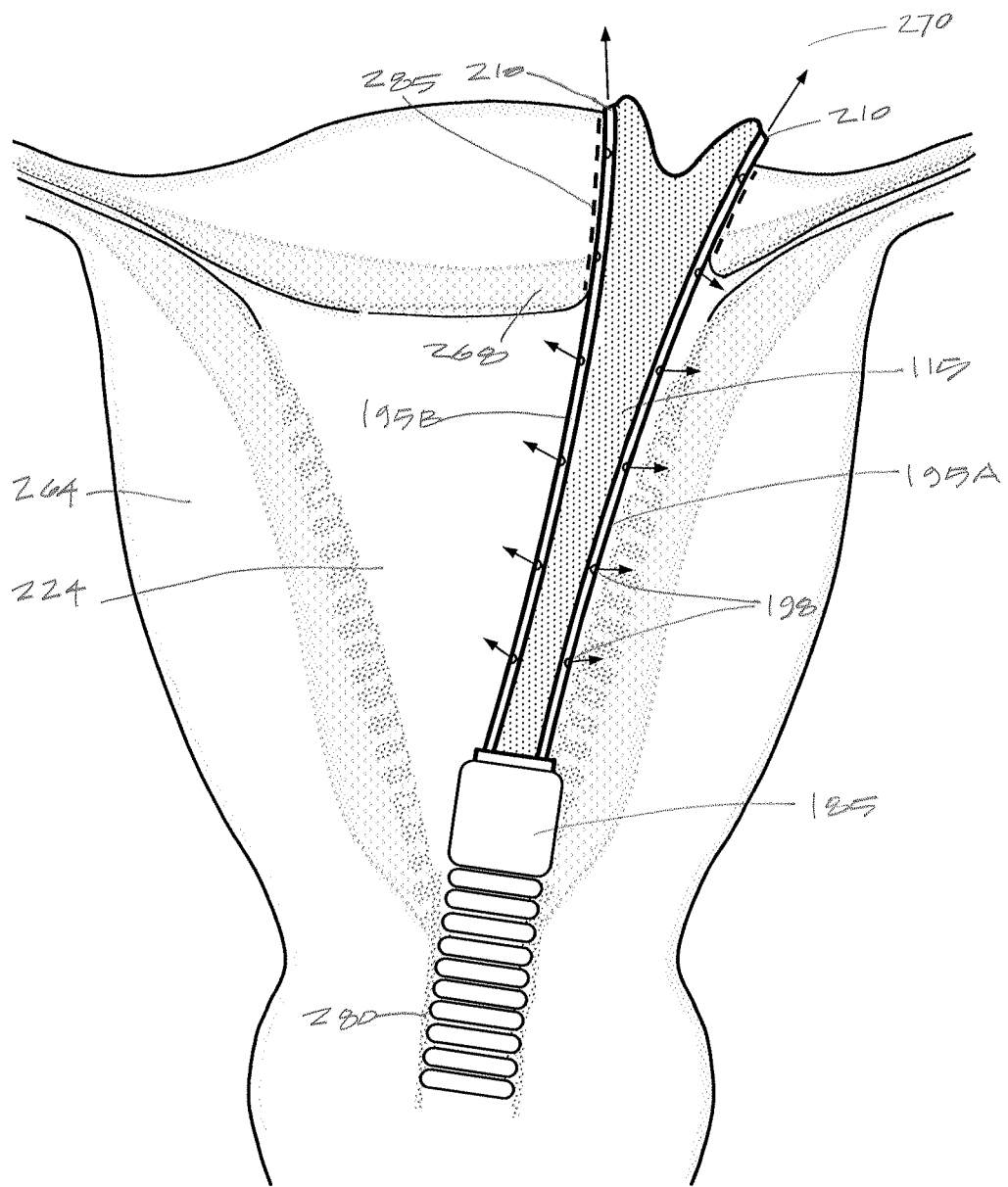
FIG. 6B is a schematic view similar to that of FIG. 6A, except that FIG. 6B indicates that the energy applicator has penetrated the fundus, and potentially plugs the perforation, except that unlike the prior art in FIG. 4B, the gas flow is directed though non-collapsible flow channels to the distal tip of the energy applicator and into the abdominal cavity, wherein monitoring at least one gas flow parameter will determine that there is a perforation in the uterine cavity wall.

FIGS. 6A-6B illustrate the improved systems and methods corresponding to the invention, which can solve the problem of mischaracterizing the integrity of the uterine cavity, which can occur with a prior art system as illustrated in FIG. 5B. In FIG. 6A, it can be seen that the energy applicator 115 of FIG. 2 is expanded in the patient's uterine cavity. Prior to insertion and expansion of the applicator body 115, the inflatable seal 185 was expanded in the endocervical canal 280. In FIG. 6A, it is again assumed that the physician has successfully used a probe or sound to measure the length of the uterine cavity 224 which resulted in no perforation of the uterine wall 264 with the sound. FIG. 6A shows $CO_2$ being introduced through the flow sleeves 195A and 190B and thereafter the $CO_2$ flows outwardly from outlets 198 and 210 into the uterine cavity 224. In one variation of monitoring a flow parameter, the physician actuates the system to electronically open valve 255 in the gas flow controller 165 which provides the $CO_2$ flow through the system. The gas flow controller 165 monitors the flow meter 250 therein over an interval that can range from 1 second to 60 seconds, or 5 second to 30 seconds, to determine the change in the rate of flow and/or a change in pressure. In an embodiment, the flow sensor 250 comprises a Honeywell AWM5000 Series Mass Airflow Sensor, for example Model AWM5101, that measure flows in units of mass flow. Other flow sensors may be used, such as a Honeywell AWM3000 or Honeywell Zephyr model sensor. In one embodiment, the initial flow rate is between 0.01 slpm (standard liters per minute) and 1.0 slpm, or between 0.01 slpm and 0.02 slpm. The gas flow controller 165 includes a microprocessor or programmable logic device that provides a feedback signal from the flow meter indicating that either (i) the flow rate has dropped to zero or close to zero to thus characterize the uterine cavity as non-perforated, or (ii) the flow rate has not dropped to a predetermined threshold level within a predetermined time interval to thus characterize the uterine cavity as perforated or that there is a failure in sealing balloon 185 or its deployment so that the cervical canal 280 is not occluded. In one embodiment, the threshold level is 0.02 slpm for characterizing the uterine cavity as non-perforated. In this embodiment, the controller provides a signal indicating a non-perforated uterine cavity if the flow drops below 0.02 slpm between a first time point, (e.g., 0.5 seconds of flow, 1 second of flow, or 2 seconds of flow) and a second time point which is a flow time-out limit, which can be 5 seconds, 10 seconds, 20 seconds or 30 seconds. If the system then characterizes the uterine cavity as non-perforated, the controller can enable actuation of energy delivery by the physician or automatically actuate energy delivery.

FIG. 6B illustrates another scenario in which the physician's use of the sound resulted in a perforation 285 in the fundus 266, similar to that depicted in use of the prior art device in FIG. 5B. Further, FIG. 6B shows that the physician's insertion of energy applicator 115 followed the path of the sound through the perforation 285 and into the abdominal 270. Thereafter, the $CO_2$ gas flow is initiated which propagates through flow channel sleeves 195A and 195B to the plurality of outlets 198 and 210 in each sleeve. As can be seen in FIG. 6B, the flow channel sleeves 195A and 190B extend over the entire length of the energy applicator 115 and it can be seen that $CO_2$ will flow (indicated by arrows 222) through some outlets 198 into the uterine cavity 224 and flow through other outlets 198 or at least terminal outlets 210 into the patient's abdominal cavity 270. In this situation, even if the cross-section of the energy applicator 115 effectively plugs the perforation 285, such a perforation will be detected easily since $CO_2$ will flow unimpeded through outlets 210 into the patient's uterine cavity 270 which offers little to no resistance to such a gas inflow. Thus, if the initial flow rate is between 0.01 slpm and 1.0 slpm, or between 0.01 slpm and 0.05 slpm, as described above, such a flow will not drop to a predetermined threshold level within a predetermined time interval as described above, and the uterine cavity 224 will be characterized as being perforated. Following the determination that there exists a perforation, the physician then will know to not perform an ablation procedure. Optionally, the controller will disable energy delivery by the system.

Now turning back to FIG. 1, it can be understood from the motor 132 is operated to expand and contract the frame 130 within the energy applicator. Another feature is provided to allow for the quick release of the engagement between the motor and the interior sleeve 135 is driven by the motor. As can be seen in FIG. 1, the quick release button 288 is provided in the handle 106 which will disengage the motor from the interior sleeve 135 thus allowing the frame 132 collapse as the energy applicator is withdrawn from the uterine cavity through the cervical canal.

In another aspect of the invention relating to the motor-operated frame 130, the controller 115 can include algorithms that monitor the voltage to the motor 132 which, in effect, can determine the resistance to opening or widening the frame 130 and the energy applicator 115 and thereafter signal the physician that there may be an abnormal resistance to opening the energy applicator. The signal can be useful in informing the physician that the energy applicator is embedded in tissue, similar to that of a perforation, which could be important information for safely performing the procedure. The signal can be provided to the position by tactile feedback or aural or video signals.

Figure 7A:
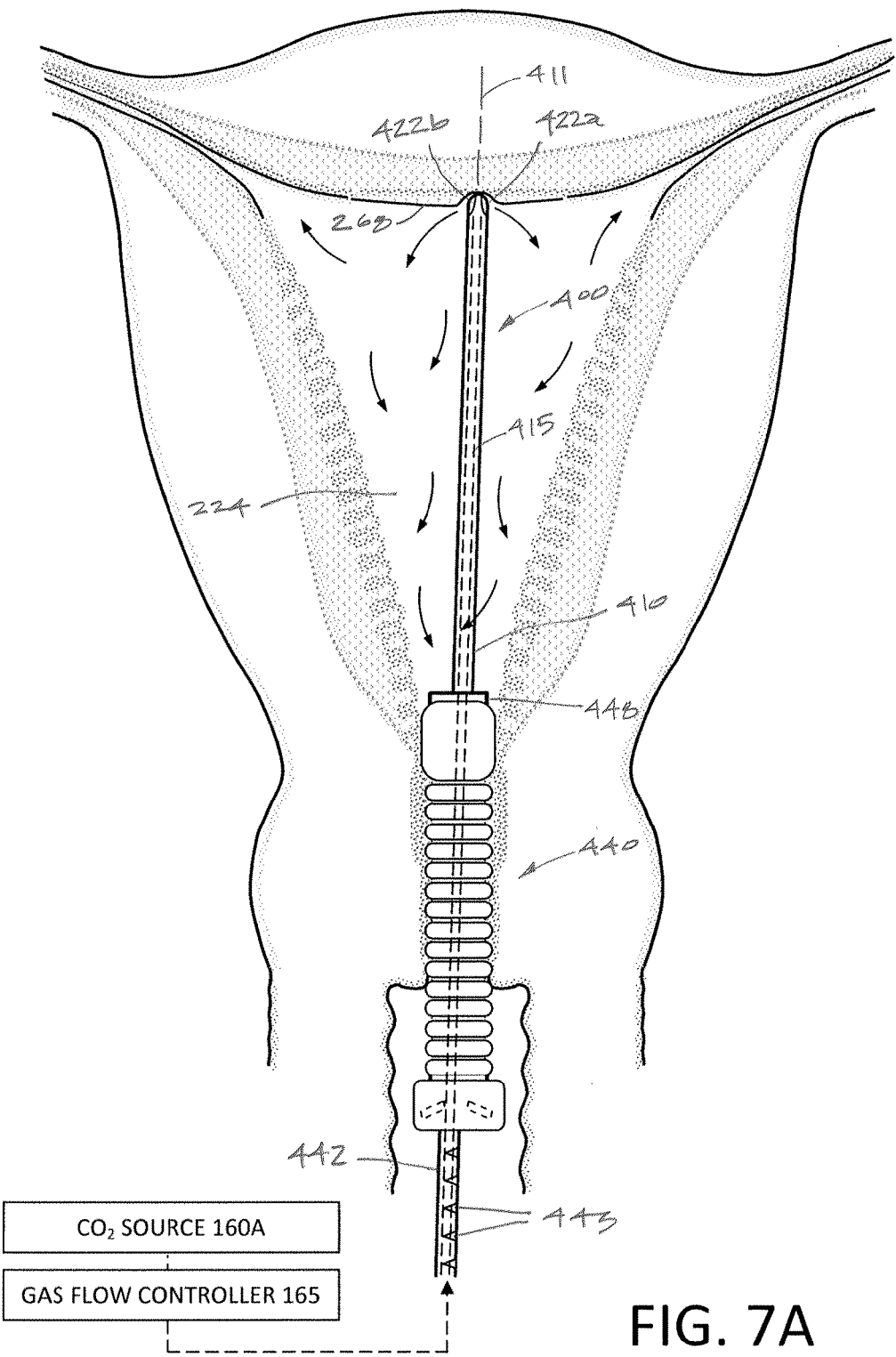
Figure 7B:
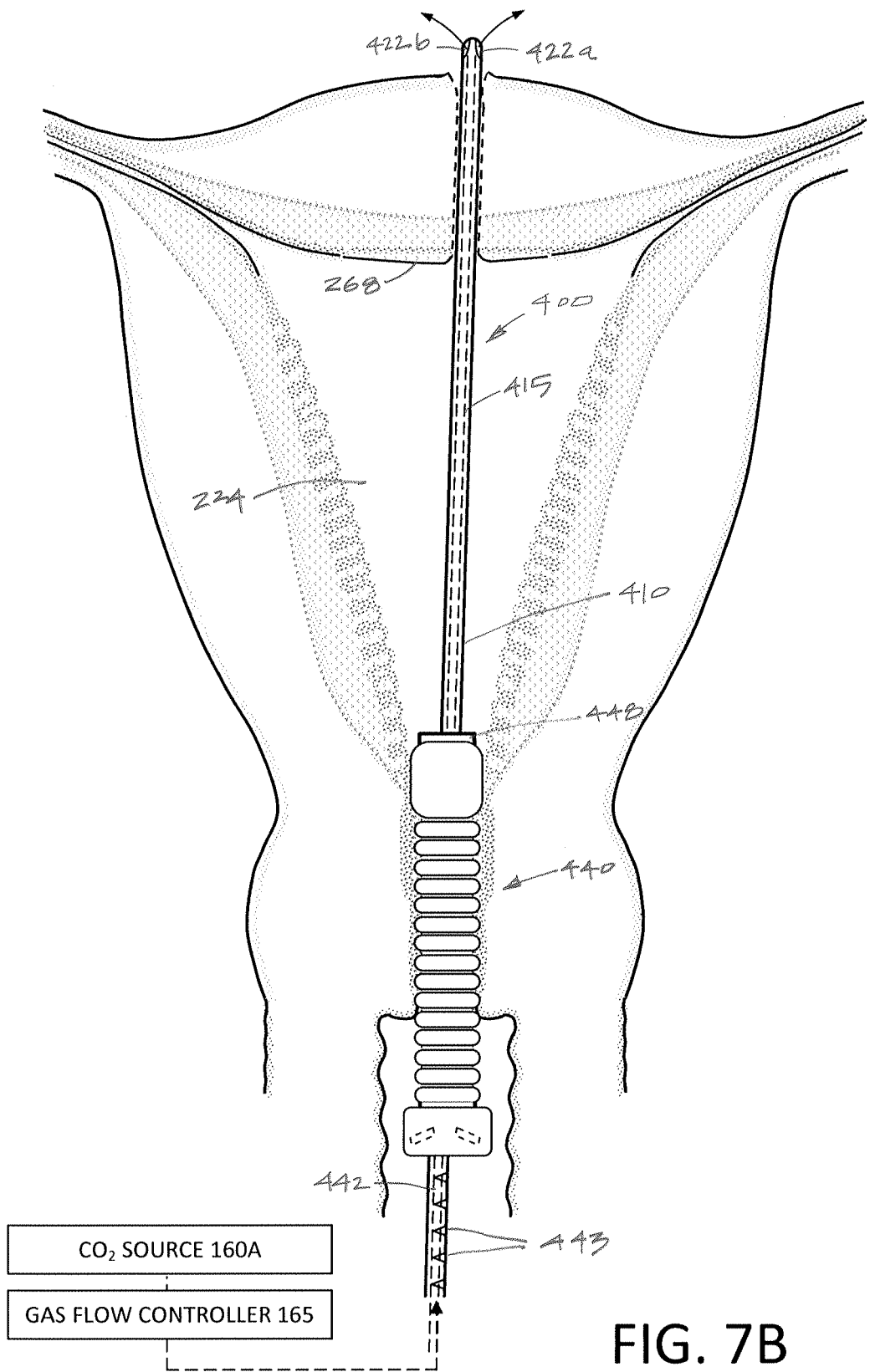
FIG. 7B is a schematic view of the probe of FIG. 7A wherein fluid flows through the probe which indicates a perforated uterine cavity.
Figure 7C:
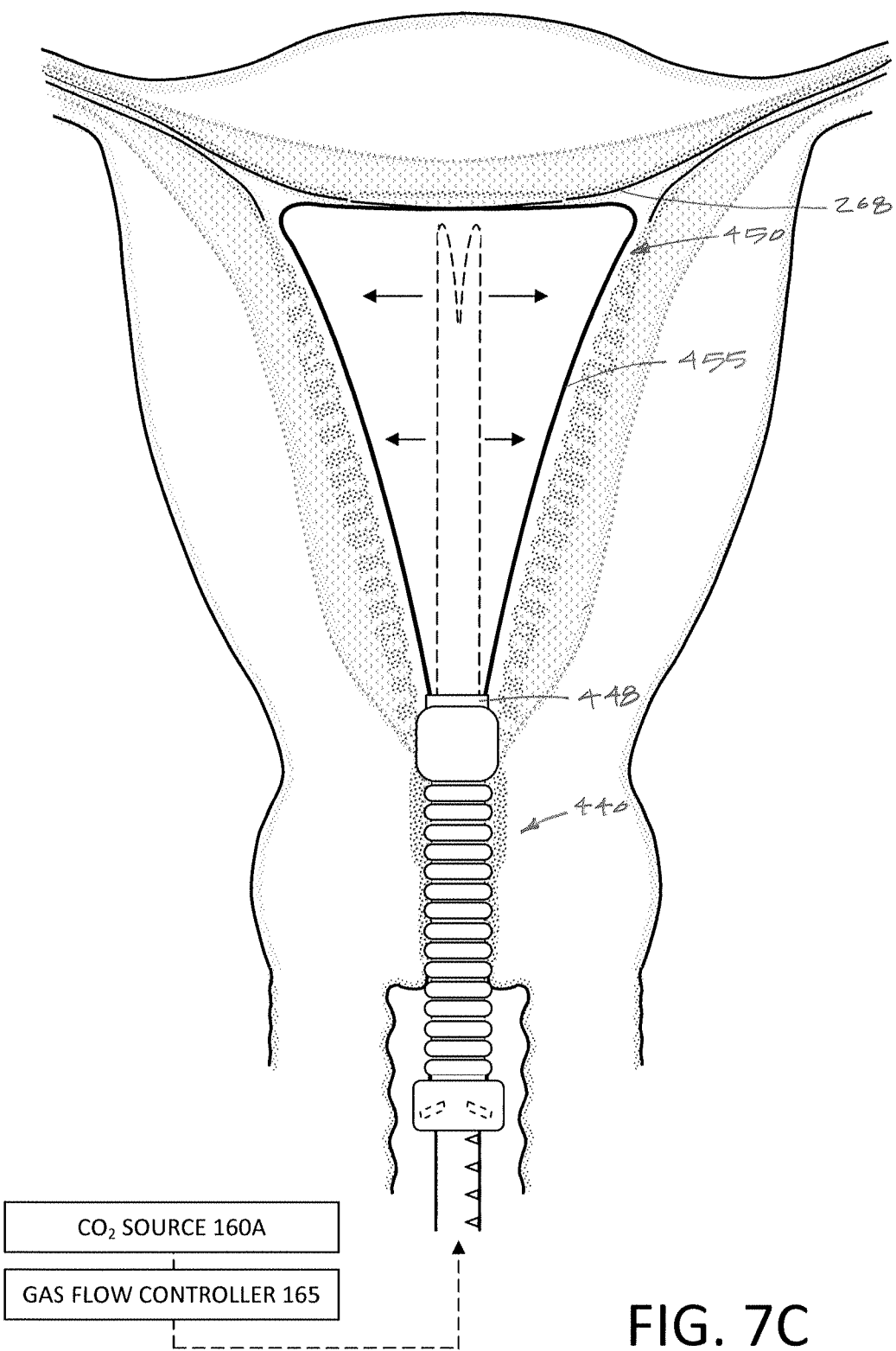
FIG. 7C is a schematic view of a step of a ablation treatment method that follows FIG. 7A wherein the measuring probe can be removed through the sealing member and an ablation probe introduced through the seal to perform an ablation procedure.

Now turning to FIGS. 7A-7C, another variation of the invention is shown which comprises an elongated probe 400 that is adapted for use as a uterine sound, or cavity length measuring device. In this variation, the probe 400 is adapted for measuring the length of the uterine cavity 224 with a dedicated instrument that does not carry an energy applicator 115. In other words, the probe 400 can be used independently in a first step or "measuring" step of the procedure, which then can be followed by a subsequent step in which an ablation device is introduced into the patient's uterine cavity to perform the ablation procedure.

In FIG. 7A, it can be seen that probe 400 has an elongated introducer portion 410 extending along axis 411 with an interior flow channel 415 therein. The flow channel 415 can be coupled to $CO_2$ source 160A and flow controller 165 as described above to provide a gas flow through flow channel 415 which extends to distal outlets 422a and 422b. In one variation, as shown in FIG. 7A, distal outlets 422a and 422b are positioned to be partially side-facing at the distal tip for 424 of the probe 400. Additional outlets can be provided near the distal tip.

FIG. 7A further shows a method using the probe 400, wherein initially a cervical sealing member 440 is positioned in the cervical canal 280. The cervical sealing member 440 can be a fluid expandable balloon as shown in FIG. 7A, or any form of resilient or foam plug as known in the prior art to substantially seal the cervical canal. The cervical sealing member 440 further includes a flexible valve, such as a duckbill valve 445 as is known in the art, for accommodating the insertion of tools therethrough while preserving a fluid seal. FIG. 7A also illustrates the step of introducing the probe 400 through the sealing member 440 into the uterine cavity 224, and providing a gas flow through fluid channel 415 which then circulates in, and expands, the uterine cavity until a preselected pressure prevents further fluid inflow. Thus, it can be understood that the controller 155 can monitor either the fluid flow rate into the uterine cavity, or the intracavity pressure, as described above to determine that there is no perforation of the uterine wall.

In FIG. 7A, it can also be seen that the proximal shaft portion 442 of the probe has dimension markings 443 which can be used as an additional safety feature to allow the physician to know the depth of the probe relative to a proximal end 448 of the sealing member 440.

Now turning to FIG. 7B, another scenario is illustrated wherein the probe 400 penetrates the fundus 268 of the uterus. This potential scenario is similar to that of FIG. 6B above wherein the energy applicator 115 of the device penetrated the fundus. In FIG. 7B, it can be seen that $CO_2$ gas will flow outwardly from distal outlets 422a and 422b into the patient's abdominal cavity 270 which offers no resistance to such a gas flow. In this situation, the controller 115 again will monitor flow parameters such as fluid flow rate and fluid pressure in the uterine cavity and will determine whether a perforation exists. More in particular, the flow rate will not drop below a threshold level over a selected time interval which then characterizes the uterus as perforated. Alternatively, the controller 115 can monitor pressure in flow channel 415 to determine that a predetermined threshold pressure is not achieved, which again would indicate that the uterus is perforated.

FIG. 7C illustrates the subsequent step of the ablation procedure wherein the measurement probe 400 is withdrawn from the cervical seal 440, and an ablation device 450 with energy applicator portion 455 is introduced through the cervical seal and the uterine cavity. Thereafter, the energy applicator is activated to complete the ablation procedure as described above. The energy applicator can be of the type described above that also includes flow channels with $CO_2$ inflows to ensure that the ablation device does not penetrate the uterine wall.

Although particular embodiments of the present invention have been described above in detail, it will be understood that this description is merely for purposes of illustration and the above description of the invention is not exhaustive. Specific features of the invention are shown in some drawings and not in others, and this is for convenience only and any feature may be combined with another in accordance with the invention.

Although particular embodiments of the present invention have been described above in detail, it will be understood that this description is merely for purposes of illustration and the above description of the invention is not exhaustive. Specific features of the invention are shown in some drawings and not in others, and this is for convenience only and any feature may be combined with another in accordance with the invention. A number of variations and alternatives will be apparent to one having ordinary skills in the art. Such alternatives and variations are intended to be included within the scope of the claims. Particular features that are presented in dependent claims can be combined and fall within the scope of the invention. The invention also encompasses embodiments as if dependent claims were alternatively written in a multiple dependent claim format with reference to other independent claims Other variations are within the spirit of the present invention. Thus, while the invention is susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein.

What is claimed is:

1. A method for accessing a patient's uterine cavity through an endocervical canal and detecting perforations in a uterus, comprising:
   providing a system including an elongated probe having a proximal shaft portion and an energy applicator, wherein the energy applicator extends distally from a distal end of the proximal shaft portion and has a distal tip, a flow channel and having a terminal outlet at the distal tip of the energy applicator and a plurality of additional outlets facing outwardly from the energy applicator, and a fluid source coupled to the flow channel;
   sealing the endocervical canal with a seal;
   trans-cervically inserting the elongated probe through the seal into the uterine cavity, wherein the distal tip is at a distal-most location on the elongated probe as the elongated probe enters the uterine cavity;
   introducing a fluid flow through the flow channel adapted to flow outwardly from the terminal outlet and the plurality of additional outlets into the uterine cavity after the distal tip of the energy applicator has been inserted, whereby the fluid flow will leak through perforations in the wall of the uterine cavity when any such perforations are present; and monitoring a parameter of said fluid flow after the distal tip of the energy applicator has been inserted to track a flow rate of fluid while the elongated probe is in the uterine cavity to detect a perforation in the uterus, wherein fluid flow though the terminal and additional outlets continues when the distal tip has penetrated the wall of the uterus but drops to zero or close to zero when there are no perforations.

2. The method of claim 1 further comprising controlling and monitoring the fluid flow using a controller.

3. The method of claim 2 wherein the controller is configured to provide the fluid inflow at a rate of between 0.01 slpm and 0.10 slpm.

4. The method of claim 2 wherein the controller is configured to monitor at least one parameter selected from the group of fluid flow rate, fluid pressure and fluid flow volume.

5. The method of claim 1 wherein the fluid flow comprises $CO_2$.

6. The method of claim 1 wherein the flow channel is configured with additional outlets spaced proximally from said terminal outlet along the length of the flow channel, wherein fluid flow is unimpeded from at least some of the outlets into the uterine cavity as the distal tip of the energy applicator is advanced in the event that some outlets become plugged.

7. The method of claim 4 further including generating a signal when the flow rate drops below a predetermined threshold minimum level over a predetermined time interval after initiation of the fluid flow to thereby characterize the uterus as not perforated.

8. The method of claim 4 further including generating a signal when the flow rate drops below a predetermined threshold minimum level to thereby characterize the uterus as not perforated.

9. The method of claim 8 wherein the predetermined level is between 0.01 and 0.05 slpm.

10. The method of claim 8 wherein the time interval is between 1 second and 20 seconds.

11. The method of claim 4 further including generating a signal when the flow rate does not drop below a predetermined threshold minimum level over a predetermined time interval after initiation of the fluid flow to thereby characterize the uterus as perforated.

12. The method of claim 11 wherein the predetermined level is between 0.01 and 0.05 slpm.

13. The method of claim 11 wherein the time interval is between 1 second and 20 seconds.

14. The method of claim 1 wherein the probe carries an energy applicator for ablating uterine tissue, wherein the terminal outlet is at a distal end of the energy applicator.

15. The method of claim 8 wherein the controller activates the energy applicator responsive to the uterus being characterized as not perforated.

16. The method of claim 11 wherein the controller prevents activation of the energy applicator responsive to the uterine cavity being characterized as perforated.

17. The method of claim 1 wherein the monitoring step includes measuring a pressure in the uterine cavity through the flow channel.

18. The method of claim 17 further including generating a signal when the measured pressure does not remain above a predetermined threshold level for a predetermined time interval to characterize the uterus as perforated.

19. The method of claim 18 further including a step of determining when the monitored pressure does remain above a predetermined threshold level for a predetermined time interval to characterize the uterus as not perforated.

20. A system for endometrial ablation comprising:
an elongated probe configured for trans-cervical introduction to a uterine cavity through a cervical seal, the probe extending along a longitudinal axis to a distal end and having a proximal shaft portion;
an applicator head for ablating uterine tissue, said applicator head extending distally from a distal end of the proximal shaft portion and having an interior and an exterior; and
a flow channel on the applicator head and having a terminal outlet in a distal tip thereof and a plurality of additional outlets extending along a side thereof and facing outwardly from the applicator head, wherein the terminal outlet and the plurality of additional outlets open to the exterior of the applicator head;
a pressurized fluid source adapted to deliver a fluid flow through the flow channel, wherein fluid flow from the terminal and additional outlets is unimpeded into the uterine cavity when the applicator head is in the uterine cavity; and
a controller configured to monitor at least one fluid flow parameter from a monitoring mechanism selected from the group of a flow rate meter, a pressure sensor and a flow volume meter.

21. The system of claim 20 wherein the controller is configured to provide the fluid flow at a rate of 0.01 slpm, to 0.10 slpm.

22. The system of claim 20 wherein the applicator head comprises an elastomeric wall which is expandable to a triangular shape and which has a first flow channel extending along one outside wall surface and a second flow channel extending along an opposite outside wall surface.

23. The system of claim 22 wherein the applicator head is configured to ablate uterine tissue with heat.

24. The system of claim 23 wherein the applicator head comprises at least one of an RF device, a heated fluid device, a light energy device, a resistive heat device, and inductive heating device, an ultrasound device, or a heated vapor device.

25. The system of claim 22 wherein the applicator head is configured to ablate uterine tissue cryogenically.

26. The system of claim 20 further comprising the cervical seal, wherein the cervical seal is configured to prevent fluid leakage outwardly from the uterine cavity through the cervical canal.

27. The system of claim 20 wherein the applicator head includes a portion that is expandable to a triangular shape with first and second flow outlets at distal tips of said triangular shape.

28. The system of claim 20 wherein the number of flow outlets ranges from 2 to 100.

29. The system of claim 20 wherein a flow outlet is configured to face at least one of distally, upwardly and downwardly.

* * * * *